(12) United States Patent
Jourdainne

(10) Patent No.: US 10,775,297 B2
(45) Date of Patent: Sep. 15, 2020

(54) LASER ABSORPTION SPECTROSCOPY SYSTEM AND METHOD FOR DISCRIMINATION OF A FIRST AND A SECOND GAS

(71) Applicant: EcoTec Solutions, Inc., Colton, CA (US)

(72) Inventor: Laurent Jourdainne, Stutzheim-Offenheim (FR)

(73) Assignee: EcoTec Solutions, Inc., Colton, CA (US)

(*) Notice: Subject to any disclaimer, the term of this patent is extended or adjusted under 35 U.S.C. 154(b) by 346 days.

(21) Appl. No.: 15/446,878

(22) Filed: Mar. 1, 2017

(65) Prior Publication Data

US 2018/0059003 A1 Mar. 1, 2018

Related U.S. Application Data

(60) Provisional application No. 62/378,994, filed on Aug. 24, 2016.

(51) Int. Cl.
*G01N 21/01* (2006.01)
*G01N 21/359* (2014.01)
(Continued)

(52) U.S. Cl.
CPC .............. *G01N 21/01* (2013.01); *G01J 3/427* (2013.01); *G01K 13/00* (2013.01); *G01M 3/202* (2013.01); *G01M 3/22* (2013.01); *G01N 21/031* (2013.01); *G01N 21/31* (2013.01); *G01N 21/3504* (2013.01); *G01N 21/359* (2013.01);
(Continued)

(58) Field of Classification Search
None
See application file for complete search history.

(56) References Cited

U.S. PATENT DOCUMENTS

2008/0123712 A1   5/2008 Zhou et al.
2012/0062895 A1*  3/2012 Rao .................. G01N 21/39
                                                      356/437
(Continued)

FOREIGN PATENT DOCUMENTS

WO   WO 1993/015391 A1   8/1993
WO   WO 2004/023114 A1   3/2004

OTHER PUBLICATIONS

Extended European Search Report for 17187635.2 dated Jan. 2, 2018 in 28 pages.

*Primary Examiner* — Paul M. West
*Assistant Examiner* — Mark A Shabman
(74) *Attorney, Agent, or Firm* — Knobbe Martens Olson & Bear, LLP

(57) ABSTRACT

A system and method to discriminate between a first preselected gas and at least one other preselected gas use of an absorption spectroscopy analyzer that includes a Herriott cell and a temperature sensitive light source. The light source operates at a temperature that emits a beam at a wavelength that corresponds to high absorption by a first preselected gas. When a predetermined level of this gas is detected in a gas sample, the analyzer changes the operating temperature of the light source to emit a beam at a wavelength that corresponds to high absorption by a second preselected gas. The second preselected gas can be a different isotope of the first preselected gas.

13 Claims, 5 Drawing Sheets

(51) Int. Cl.
*G01J 3/427* (2006.01)
*G01N 21/03* (2006.01)
*G01M 3/20* (2006.01)
*G01N 21/3504* (2014.01)
*G01M 3/22* (2006.01)
*G01N 21/39* (2006.01)
*G01K 13/00* (2006.01)
*G01N 21/31* (2006.01)
*G01N 33/00* (2006.01)
*G01J 3/42* (2006.01)
*G01J 3/433* (2006.01)

(52) U.S. Cl.
CPC .......... *G01N 21/39* (2013.01); *G01N 33/004* (2013.01); *G01N 33/0037* (2013.01); *G01N 33/0044* (2013.01); *G01N 33/0054* (2013.01); *G01J 2003/423* (2013.01); *G01J 2003/4334* (2013.01); *G01N 2021/399* (2013.01); *G01N 2201/0221* (2013.01); *G01N 2201/062* (2013.01); *G01N 2201/066* (2013.01); *G01N 2201/0612* (2013.01); *G01N 2201/1241* (2013.01)

(56) References Cited

U.S. PATENT DOCUMENTS

| | | | |
|---|---|---|---|
| 2012/0287418 A1* | 11/2012 | Scherer | G01N 21/61 356/51 |
| 2013/0044314 A1* | 2/2013 | Koulikov | G01N 21/1702 356/72 |
| 2014/0034840 A1* | 2/2014 | Davenport | G01J 3/42 250/370.01 |
| 2016/0266034 A1* | 9/2016 | Helbley | G01N 21/3504 |

* cited by examiner

LASER ABSORPTION SPECTROSCOPY SYSTEM AND METHOD FOR DISCRIMINATION OF A FIRST AND A SECOND GAS

INCORPORATION BY REFERENCE TO ANY PRIORITY APPLICATIONS

This application claims the benefit of U.S. Provisional Application Ser. No. 62/378,994, filed Aug. 24, 2016, entitled "LASER ABSORPTION SPECTROSCOPY SYSTEM AND METHOD FOR DISCRIMINATION OF A FIRST AND A SECOND GAS," which is hereby incorporated by reference in its entirety and for all purposes.

FIELD

The present disclosure relates generally to gas detection and analysis. In particular, the invention relates to portable laser absorption spectroscopy systems and methods used to distinguish between two or more different types of gas, such as during a leak survey.

BACKGROUND

A known and successful system for detecting small quantities of gas in the environment is by the use of absorption spectroscopy (see U.S. Pat. No. 7,352,463 B2 to Bounaix, hereby incorporated by reference herein and included herein as Appendix A) and portable analyzers that incorporate this technique in combination with a Herriott cell are commercially available (see GAZOMAT™ INSPECTRA® natural gas leak portable analyzer). By this technique, a light beam of a selected frequency that is highly absorbed by the particular gas for which the instrument is designed is passed through a sample of the gas. The rate of absorption of the light beam is used as an indicator of the level of concentration of the gas in the sample. To increase the light beam's length of travel through the gas, the Herriot (multi-path) cell is used.

The particular gas can be methane, butane, propane, ethane, oxygen, hydrogen, nitrogen, water vapor, hydrogen fluoride, hydrogen chloride, hydrogen bromide, hydrogen sulfide, ammonia, carbon monoxide, carbon dioxide, nitrogen oxide, nitrogen dioxide, sulfur hexafluoride, or another gas of interest. For example, the level of concentration of methane in a gas sample can be determined by initiating a light beam at a frequency that is highly absorbed by methane and passing the beam through the gas sample. To determine whether the methane is from a natural gas or a biogas source requires further discrimination.

Discrimination of natural gas and biogas is accomplished using either gas chromatography systems or cavity ringdown spectroscopy ("CRDS"). Gas chromatography involves a long response time, is not very sensitive, and requires regular calibration. CRDS is expensive and can only be used with a leak survey car.

A need exists for an absorption spectroscopy system and method that can detect a first gas, like methane, and then immediately shift to detect two or more isotopes of that gas or detect an entirely different second gas.

SUMMARY

The systems and methods of this disclosure each have several innovative aspects, no single one of which is solely responsible for its desirable attributes. Without limiting the scope as expressed by the claims that follow, its more prominent features will now be discussed briefly.

In some embodiments, a method of measuring a concentration in an environment of at least a first preselected gas and a second preselected gas is described. The method may include continuously moving a stream of a sample gas from the environment through a confined testing area within a detecting instrument, energizing a light source of the detecting instrument at a first operating temperature to produce a light beam at a first preselected wavelength for absorption by the first preselected gas, measuring the absorption of the light beam at the first preselected wavelength to provide an indication of a concentration of the first preselected gas within the sample gas, energizing the light source at a second operating temperature to produce a light beam at a second preselected wavelength for absorption by the second preselected gas, and measuring the absorption of the light beam at the second preselected wavelength to provide an indication of a concentration of the second preselected gas within the sample gas. As noted in further detail below, adjustments in operating temperature of a light source may be accomplished by energizing the light source (e.g., adjusting current level provided to the light source) to the desired operating temperature and/or activating a heating or cooling element to adjust temperature of the light source to the desired operating temperature.

At least one of the first and second preselected gases can be selected from methane ($CH_4$), ethane ($C_2H_6$), propane ($C_3H_8$), butane ($C_4H_{10}$), oxygen ($O_2$), hydrogen ($H_2$), nitrogen (N), water ($H_2O$), hydrogen fluoride (HF), hydrogen chloride (HCl), hydrogen bromide (HBr), hydrogen sulfide ($H_2S$), ammoniac ($NH_3$), ammonia ($NH_4$), carbon monoxide (CO), carbon dioxide ($CO_2$), nitrogen monoxide (NO), nitrogen dioxide ($NO_2$), sulfur hexafluoride ($SF_6$), tetrahydrothiophene ($C_4H_8S$), and tert-butyl mercaptan ($C_4H_{10}S$).

The second preselected gas can be an isotopologue of the first preselected gas. The first preselected gas and the second preselected gas can be isotopologues of methane.

The light source can be configured to transition between the first operating temperature and the second operating temperature in less than 10 seconds. The light source can be a laser diode. The light source can be a light emitting diode. The absorption of the light beam at the first preselected wavelength and the absorption of the light beam at the second preselected wavelength can be measured at a photodetector.

The method can further comprise energizing an operating temperature of the photodetector. The operating temperature of the photodetector can be controlled based on at least one of the first and second operating temperatures. The detecting instrument can further include a multi-pass cell.

The light source can be energized at the second operating temperature based at least in part on the indication of the concentration of the first preselected gas. The light source can be energized at the second operating temperature responsive to the indication of the concentration of the first preselected gas exceeding a predetermined threshold.

In another embodiment, a method of measuring a concentration in an environment of at least a first preselected gas and a second preselected gas is described. In this embodiment, the method may include continuously moving a stream of a sample gas from the environment through a confined testing area within a detecting instrument, energizing a light source of the detecting instrument to produce a light beam at a wavelength that corresponds to an absorption line of a gas, and energizing a photodetector at a first operating temperature to detect absorption of the light beam by the first preselected gas.

The method can further include energizing the photodetector at a second operating temperature to detect absorption of the light beam by the second preselected gas and measuring the absorption of the light beam to provide an indication of a concentration of the second preselected gas at the preselected wavelength. The method can further include energizing the light source at a first operating temperature to produce a light beam at a preselected wavelength for absorption by the first preselected gas. The method can further include energizing the light source at a second operating temperature to produce a light beam at a preselected wavelength for absorption by the second gas.

In some embodiments a method of measuring a concentration in an environment of a preselected gas is described. In this embodiment, the method may include continuously moving a stream of a sample gas from the environment through a confined testing area within a detecting instrument, energizing a light source of the detecting instrument to produce a light beam at a wavelength that corresponds to an absorption line of a reference gas, energizing the light source at a first operating temperature to produce a light beam at a preselected wavelength for absorption by a first preselected gas, the preselected wavelength being a different wavelength than the wavelength corresponding to the absorption line of the reference gas, and measuring the absorption of the light beam to provide an indication of a concentration of the first preselected gas at the preselected wavelength.

The method can further include energizing the light source at a second operating temperature to produce a light beam at a preselected wavelength for absorption by a second preselected gas, and measuring the absorption of the light beam to provide an indication of a concentration of the second preselected gas at the preselected wavelength.

In some embodiments, an absorption spectroscopy system and method to discriminate between at least a first and a second gas, or between at least a first isotope and a second isotope of a same gas, changes the working or operating temperature of the light beam's source between that of a first light beam of a selected frequency that is highly absorbed by the first gas and that of a second light beam of selected frequency that is highly absorbed by the second gas. Preferably, the system and method make use of a detection instrument that includes a Herriott (multi-pass) cell.

In some embodiments of the system and method, a stream of sample gas is continuously moved from the environment through a confined testing area located with the detection instrument; a light source is energized to emit a light beam in a range of frequencies that correspond to an absorption line of some gas (that is to be detected); the operating temperature of the light source is then energized to produce a light beam at a preselected frequency for absorption by a preselected gas, the absorption is measured by way of a photodetector (or its equivalent) to provide an indication of the concentration of the preselected gas at the preselected frequency, and the operating temperature of the light source is then energized to produce a light beam at a preselected frequency for absorption by another preselected gas. The light source can be a laser diode or a light emitting diode ("LED").

The change in operating temperature, which preferably takes less than 10 seconds, can be a conditional shift, for example, dependent on whether the first gas is detected, a cyclical or regularly occurring shift, or an operator-determined shift. The operating temperature also can be shifted to detect a third preselected gas and then another (and so on). The preselected gas can be isotopes of the same group of gas.

In some embodiments, the operating temperature of a photodetector arranged to receive the light beam can be managed in correlation with that of the light source to increase the sensitivity of detection for the preselected gas. Optionally, the operating temperature of the photodetector can be changed independent of that of the light source.

In some embodiments, the various systems discussed herein may perform a method including moving a stream of sample gas from the environment through a confined testing area within a detecting instrument (e.g., continuously pushing or pulling air through the testing area); energizing a light source at a first operating temperature to produce a first light beam at a frequency that corresponds to a high degree of absorption by a first preselected gas; splitting the first light beam into multiple components (e.g., three or more); passing a first component of the first light beam to a first photo detector for providing a first electrical signal indicative of the intensity of the first light beam; passing a second component of the first light beam multiple times through the confined testing area and then to a second photo detector for providing a second electrical signal indicative of a concentration measurement corresponding to a lower concentration level; passing a third component of the first light beam over a reduced length path through the confined testing area and then to a third photo detector for providing a third electrical signal indicative of a concentration measurement corresponding to a higher concentration level; and using the first, second, and third electrical signals for determining the concentration level of the first preselected gas in the stream of sample gas. This embodiments may further include energizing the light source at a second operating temperature to produce a second light beam at a frequency that corresponds to a high degree of absorption by a second preselected gas; splitting the second light beam into multiple components; passing a first component of the second light beam to the first photo detector for providing a first electrical signal indicative of the intensity of the second light beam; passing a second component of the second light beam multiple times through the confined testing area and then to the second photo detector for providing a second electrical signal indicative of a concentration measurement corresponding to a lower concentration level; passing a third component of the second light beam over a reduced length path through the confined testing area and then to the third photo detector for providing a third electrical signal indicative of a concentration measurement corresponding to a higher concentration level; and using the first, second, and third electrical signals for determining the concentration level of the second preselected gas in the stream of sample gas.

Objectives of this invention including providing an absorption spectroscopy system and method that can automatically shift between detection of a first preselected gas and at least one other preselected gas or shift between detection of a first isotope and at least one other isotope of a same gas.

BRIEF DESCRIPTION OF THE DRAWINGS

The above-mentioned aspects, as well as other features, aspects, and advantages of the present technology will now be described in connection with various implementations, with reference to the accompanying drawings. The illustrated implementations are merely examples and are not intended to be limiting. Throughout the drawings, similar symbols typically identify similar components, unless context dictates otherwise.

NUMBERING AND ELEMENTS USED IN THE DRAWINGS AND DETAILED DESCRIPTION

Figure 1:
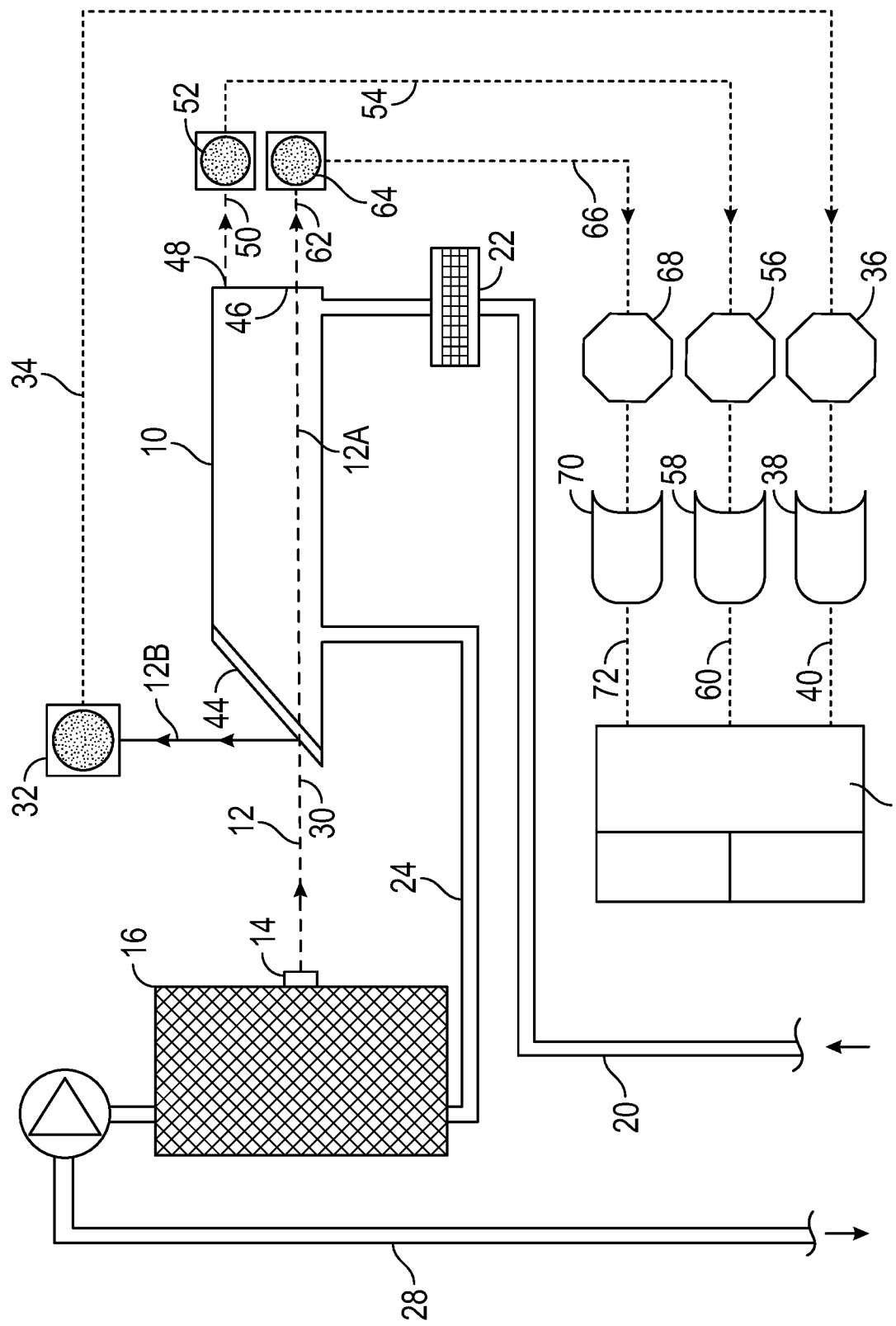
FIG. 1 is a schematic of the basic elements of one embodiment of an absorption spectroscopy analyzer.
Figure 2:
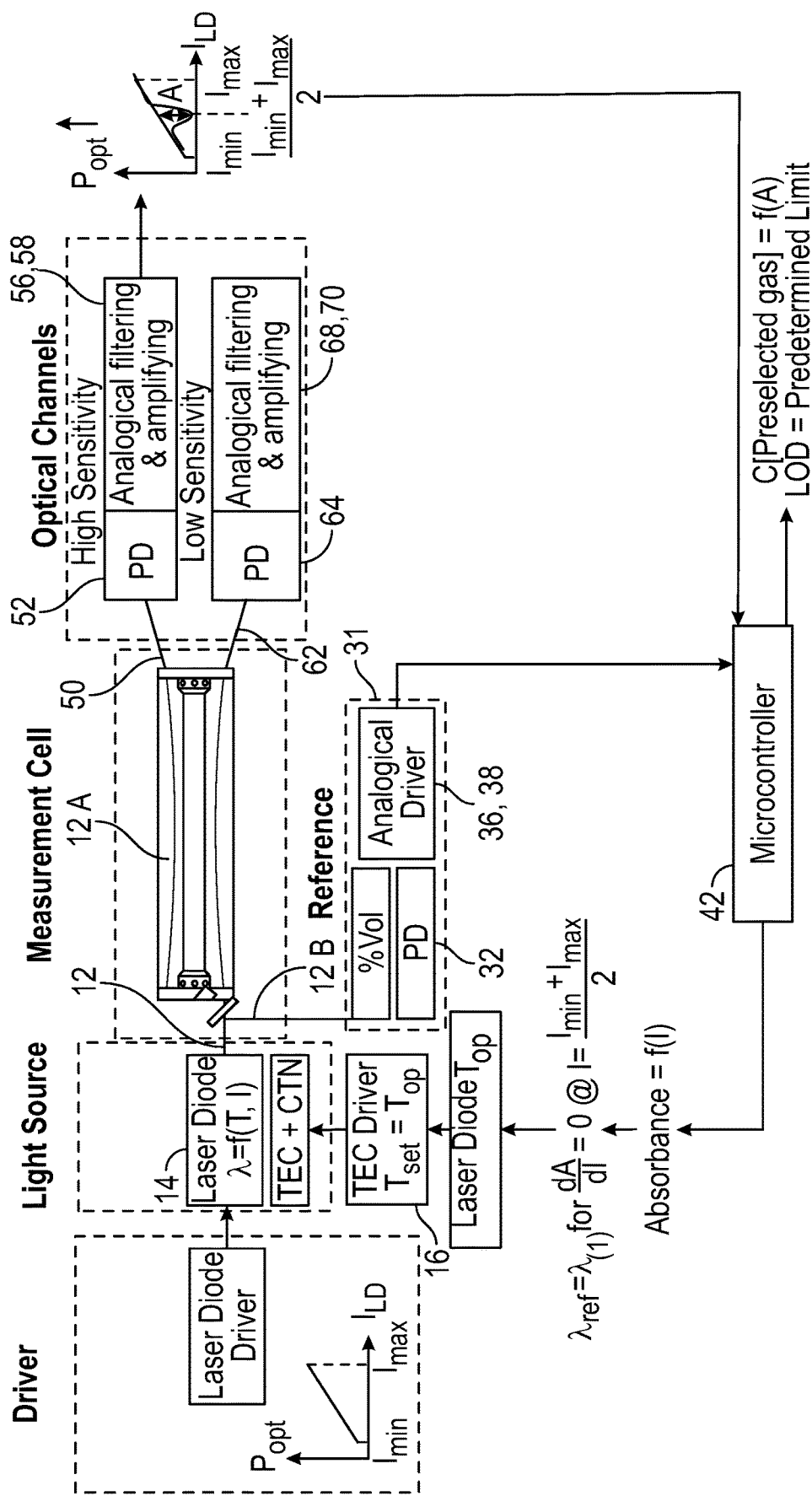
FIG. 2 is another schematic of an example embodiment of the analyzer of FIG. 1.

The following reference numerals are used in FIGS. 1 and 2 and accompanying description.
- 10 Herriott cell (confined testing area of detection instrument or analyzer)
- 12 Light beam
- 12A Portion of 12 entering 10
- 12B Portion of 12 reflected away from 10
- 14 Light beam source (laser diode or light emitting diode or their equivalent)
- 16 Temperature regulating system
- 20 Inlet tube
- 24 Outlet tube
- 28 Discharge tube
- 30 Aperture or window in 44
- 31 Reference cell
- 32 First photodetector
- 34 Conductor
- 36 Amplifier
- 38 Analog-to-digital convertor
- 40 Conductor
- 42 Microprocessor
- 44 First mirror
- 46 Second mirror
- 48 Aperture or window in 46
- 50 Exit beam (long path)
- 52 Third photodetector (high sensitivity)
- 54 Conductor
- 56 Amplifier
- 58 Analog-to-digital convertor
- 60 Conductor
- 62 Exit beam (short path)
- 64 Second photodetector (low sensitivity)
- 66 Conductor
- 68 Amplifier
- 70 Analog-to-digital convertor
- 72 Conductor

DETAILED DESCRIPTION

The following description is directed to certain implementations for the purpose of describing the innovative aspects of this disclosure. However, a person having ordinary skill in the art will readily recognize that the teachings herein can be applied in a multitude of different ways. The described implementations may be implemented in any gas detection and/or analysis system.

In some embodiments, a portable absorption spectroscopy system automatically discriminates between detection of a first preselected gas and a second preselected gas by changing the operating temperature "$T_{op}$" of a light source between a first operating temperature $T_{op(1)}$ to a second operating temperature $T_{op(2)}$. When at the first operating temperature $T_{op(1)}$, the light source emits a first light beam of a selected frequency "$f_{(1)}$" that is highly absorbed by the first preselected gas. When at the second operating temperature $T_{op(2)}$, the light source emits a second light beam of a selected frequency "f(2)" that is highly absorbed by the second preselected gas. Light of frequency $f_{(1)}$ can equally be characterized as having a wavelength $\lambda_{(1)}$, where $\lambda_{(1)}=c/f_{(1)}$. Similarly, light of frequency $f_{(2)}$ can equally be characterized as having a wavelength $\lambda_{(2)}$, where $\lambda_{(2)}=C/f_{(2)}$.

In certain embodiments, the shift in frequency or wavelength relative to this temperature shift can be characterized by:

$$d\lambda/dT=(0.1 \text{ nm})/°\text{ C.} \qquad (\text{Eq. 1}),$$

where $d\lambda/dT$ is the rate of change in the emitted wavelength with respect to the temperature of the light source. In various embodiments, the rate of change $d\lambda/dT$ may be greater or less than 0.1 nm/° C., depending on the electrical and/or thermal properties of each light beam source. In addition, the rate of change $d\lambda/dT$ of an individual light beam source may vary across the range of operating temperatures. Thus, one or more lookup tables may be generated based on experimentally determined operating temperatures associated with known wavelengths.

Figure 3:
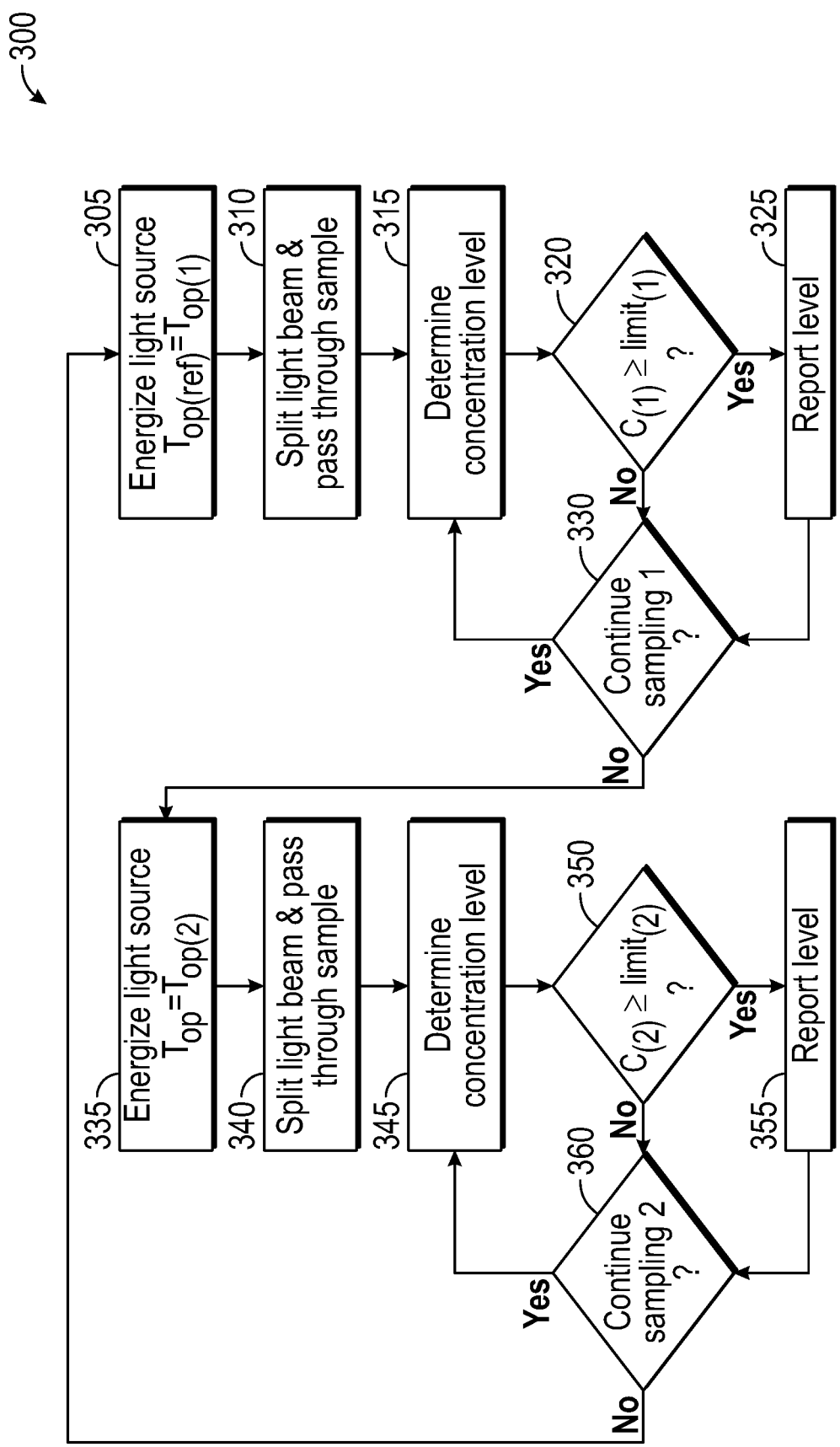
FIG. 3 is a flow diagram of an example embodiment of a method to discriminate between a first and a second preselected gas or between preselected isotopes of the same gas.

The shift from the first operating temperature $T_{op(1)}$ to the second operating temperature $T_{op(2)}$ can be a conditional shift, for example, occurring when the first gas is detected at or above a predetermined detection limit (see e.g. FIG. 3). A return from the second operating temperature $T_{op(2)}$ to the first operating temperature $T_{op(1)}$ can also be a conditional shift, for example, occurring after the second gas is detected at or above its predetermined detection limit or after a predetermined period of time during which no second gas is detected. Preferably, the time required to shift between the first and second operating temperatures, and therefore between the different frequencies or wavelengths, is 10 seconds or less, more preferably a few seconds or less and, even more preferably, no more than 2 seconds.

The first preselected gas can be methane, butane, propane, ethane, oxygen, hydrogen, nitrogen, water vapor, hydrogen fluoride, hydrogen chloride, hydrogen boride, hydrogen sulfide, ammonia, carbon monoxide, carbon dioxide, nitrogen oxide, nitrogen dioxide, sulfur hexafluoride, tetrahydrothiophene, tert-butyl mercaptan, or another gas of interest. The second preselected gas can be selected from that same group of gases, being either an entirely different gas than the first preselected gas (e.g. the first gas being $CH_4$, the second gas being $C_2H_6$) or a different isotope than that of the first preselected gas (e.g. the first gas being $^{12}CH_4$, the second gas being $^{13}CH_4$).

A laser absorption spectroscopy analyzer like that disclosed in U.S. Pat. No. 7,352,463 B2 to Bounaix, incorporated herein by reference, can be modified so that the analyzer shifts the operating temperature of the light beam's light source. In this way, discrimination between the two gases or isotopes of the same gas occurs within a single setup.

FIG. 1 is a block diagram of an example laser absorption spectroscopy analyzer. In this example, the analyzer includes a cell 10 that will be described in detail subsequently, and that provides an environment in which a light beam 12 passes through a gas sample and in which absorption of the light beam is measured.

In the various embodiments discussed herein, a light beam is provided by a laser diode, in which case light beam 12 is a laser light beam. However, the various systems and methods discussed herein can be practiced using a light source that provides a non-coherent light beam. An example of a non-coherent light source is a light emitting diode (LED). A laser diode provides a coherent light beam that is a beam of substantially uniform frequency light having the characteristic that the laser light beam does not disperse to the same extent as a non-coherent light beam. The use of a laser beam, such as produced by a laser diode, is advantageous, but the use of a laser diode is not indispensable. However, laser diodes are expensive compared to LEDs. In some applications, LEDs work satisfactorily. As used throughout this description, "laser beam" or "laser diode" are inclusive of "light beam" or "LED."

Supported to cell 10 is a structure that includes a laser diode 14 that, when energized, produces laser beam 12. Laser diodes of the type represented by 14 are temperature sensitive. That is, the frequency of the laser light produced by diode 14 varies according to the temperature of the diode. For measurement accuracy it is important that the frequency of laser beam 12 be controlled within a fairly narrow range, which in turn means that the temperature of laser diode 14 must be controlled. For this purpose, a temperature regulating system generally indicated by the block 16 is employed and will be described in detail subsequently.

The analyzer functions by moving laser beam 12 through a gas sample and determining the level of concentration of a selected gas in the gas sample by measuring absorption of the laser beam. This technology is generally referred to as "laser absorption spectroscopy." Cell 10, including the components secured in relation to it, provide a tunable laser diode absorption spectroscope. Flow channels are provided by which a gas sample is moved through cell 10. Sample gas is taken in through an inlet 18 in inlet tube 20 and flows through filter 22 into the interior of cell 10. The gas flows through cell 10 to an outlet tube 24 that connects with temperature regulating system 16. In this example, gas is moved through the system by means of a gas pump 26 to a discharge tube 28 by which the gas sample is returned to the environment.

In this embodiment, laser beam 12 passes through a window. A portion of the beam passes through an aperture 30 in a first mirror 44. The number 12A represents the first pass of the beam internally of cell 10. A portion of laser beam 12 is reflected by the window, the reflected beam being indicated by the numeral 12B. A photo detector 32 is placed to receive the interception of reflected beam 12B and provides an electrical signal that is representative of the intensity of laser beam 12. The electrical signal from photo detector 32 is conveyed by conductor 34 to an amplifier 36 that feeds into an analog to digital converter circuit 38 that provides a referenced digital input over conductor 40 that feeds into a microcontroller 42.

In many of the examples discussed herein, cell 10 is of a type generally known as a "Herriott" cell. This name is derived from the inventor of a cell that employs opposed mirrors that reflect a light beam back and forth between them so that a relatively long path can be obtained in a relatively shorter length instrument, and in which the path is in a circular pattern. While generally of the "Herriott" type, cell 10 has many improvements and innovations as will be described subsequently in detail. Furthermore, other types of detection cells may be used.

In the example of FIG. 2, cell 10 employs a first mirror 44 and an opposed second mirror 46. A small aperture 30 is provided in first mirror 44 through which the laser beam passes and forms beam 12A within the cell that first impacts second mirror 46. Beam 12A is reflected sequentially between mirrors 44 and 46 a number of times before exiting second mirror 46 through a small aperture 48. The exit beam 50 impinges on a second photo detector 52 that provides a signal on conductor 54 feeding an amplifier circuit 56 that feeds a second analog to digital converter 58 that provides a digital signal on conductor 60 leading to microcontroller 42.

As noted above, the methods and systems disclosed herein may be used to detect selected gasses such as methane, butane, propane, ethane, oxygen, hydrogen, nitrogen, $H_2O$, hydrogen fluoride, hydrogen chloride, hydrogen boride, hydrogen sulfide, ammonia, CO, $CO_2$, NO, $NO_2$ and $SF_6$. The system can be adapted to detect different selected gases by changing out the laser diode to one that produces the frequency of light most readily absorbed by the gas of interest. When a light emitting diode (rather than a laser diode) is used, the broader spectrum of light produced by it can detect more different gases but usually at higher concentrations. In some implementations, the systems disclosed herein will be described in the context of detecting methane gas, since methane is the basic component of natural gas and most manufactured fuel gasses. If a leak occurs in a gas distribution system, it can usually be located by detecting the presence of methane. Therefore, cell 10 may employ a laser diode 14 that produces a beam characterized by a frequency that corresponds to a high degree of absorption by methane. Sample gas that is drawn in through inlet 18 and flows by way of inlet tube 20 into and through cell 10 absorbs, that is, decreases the intensity of light beam 12A in proportion to the quantity of methane contained in the sample gas.

In this example, light beam 50 passes out aperture 48 in second mirror 46 after having been reflected many times between mirrors 44 and 46. Undergoing multiple reflections from the time beam 12A enters cell 10 until it exits through aperture 48 means that the beam has traversed a relatively long path equal to many times the length of cell 10 which in turn means that ample provision has been made for absorption of the light beam by the presence of methane in the gas sampler.

By comparing the intensity of the signal on conductor 34 with that on conductor 54 the concentration of methane in the sample gas passing through cell 10 can be ascertained. By accurate processing within microcontroller 42 the amount of methane contained in the sample gas passing through cell 10 can be determined with great accuracy and can be expressed such as in parts per million. The presence of methane can be detected at a sensitivity down to a few parts per million or even, ideally, to a sensitivity of one or less than one part per million.

As previously stated, beam 12 emanating from laser 14 passes through a first aperture 30 in first mirror 44 to provide beam 12A within the cell. When the initial passage of laser beam 12A within cell 10 encounters second mirror 46 most of the beam intensity is reflected back towards first mirror 44 and subsequently repeatedly reflected between first mirror 44 and second mirror 46 to finally pass out through second window 48 to form exit beam 50. However, when beam 12A strikes second mirror 46 a small portion of the intensity of the beam passes through the mirror even though no aperture or window is provided since most mirrored surfaces are not 100% reflective. The portion of light beam 12A that passes through second mirror 46 provides a second exit beam 62 that engages a third photo detector 64. This produces an electrical signal on conductor 66 passing to a third amplifier 68 that feeds an analog to digital converter 70 sending a digital signal by way of conductor 72 to microcontroller 42. The employment of two separate exit beams 50 and 62 emanating from cell 10 to activate photo detectors 52 and 64 is an important attribute of the invention herein. It is apparent that only signals appearing on conductors 40 and 60 feeding microcontroller 42 are required to measure low levels of concentration of methane in the gas passing through cell 10. It is important to detect very small levels of methane in the sample gas, which is accomplished by employing a long light path for the laser beam before the beam exits through window 48, however, this arrangement fails if a broader scale of methane detection is required. If methane is present at a relatively high level in the sample gas passing through the cell the laser beam Referring to FIG. 2, the major components of an absorption spectroscopy system are illustrated that can be used to practice the discrimination method of FIG. 3. As described above with reference to FIG. 1, a gas sample flows into a measurement cell where a light beam 12 passes through the gas sample. The sample exits by way of an outlet tube—which communicates with a temperature regulating system 16—and the sample returns to the environment. The light beam 12 is produced by a temperature sensitive light beam source 14 set to operate at a reference or first operating temperature $T_{op(1)}$ to produce a light beam 12 at a frequency or wavelength $\lambda_{(1)}$ that corresponds to a high degree of absorption by the first preselected gas:

$$\lambda_{ref} = \lambda_{(1)} \text{ for } \frac{dA}{dI} = 0 \text{ at } I = \frac{I_{min} + I_{max}}{2} \quad \text{(Eq. 2)}$$

where A is absorption and I is intensity.

Because absorption A is a function of intensity I, as the presence of the first preselected gas in the gas sample increases, the intensity I of the beam 12 as it passes through the gas sample decreases proportionately. This reduced intensity beam 12 then impinges on one or more photodetectors 52, 64 where it is converted into an electrical signal 54, 66. This signal 54, 66 is compared to an electrical signal 34 from a reference cell 31 (e.g. 50% vol. $^{12}CH_4$) that includes a photodetector 32 on which beam 12 impinges without passing through the gas sample.

The operating temperature $T_{op}$ of the light source 14 can then be shifted as follows $$T_{op(2)} = T_{op(1)} + \frac{\Delta nm}{d\lambda/dT} \quad \text{(Eq. 3)}$$

$$\Delta nm = \lambda_{(1)} - \lambda_{(2)} \quad \text{(Eq. 4)}$$

where $\lambda$ is the wavelength corresponding to a frequency of high absorption for a respective preselected gas. Calibration tables can be used to determine the correct operating temperature of the light source needed to produce the desired wavelength.

For measurement accuracy the operating temperature of light beam 12 can be controlled within a narrow range. For example, the temperature can be maintained within 1° C., 0.5° C., 0.1° C., or a similar range, of the selected operating temperature $T_{op}$. This control is accomplished using a temperature regulating system 16 that includes a thermoelectric cooler ("TEC") driver. Similar means to temperature regulating system 16 can be applied to control the operating temperature of one or more of the photodetectors 32, 52, 62 and increase detection sensitivity for a preselected gas. Thus, depending on the embodiment, one or both of the temperatures of the light source and the photodetectors may be dynamically adjusted to detect particular gases. This operating temperature can be correlated with that of the light source 14. Or, optionally, only the operating temperature of one or more of the photodetectors 32, 52, 64 is changed with the operating temperature of the light source 14 being constant.

In various embodiments, the temperature regulating system 16 can include a TEC driver and/or a heating element to precisely control the operating temperature of the light source 14. In addition, some embodiments may achieve control of the temperature of the light source 14 by regulating the amount of current applied to the light source 14, thereby modifying the amount of heat generated in the circuitry of the light source 14 by resistive heating. Thus, any reference herein to a heating component may refer to a heating element external to a light source and/or the light source itself (e.g., such as in the embodiment noted above where the light source itself can provide resistive heating). In some embodiments, a light source has known temperatures at corresponding known current levels. Thus, the system discussed herein may store those relationships (e.g., in a temperature-to-current lookup table) that is usable to adjust the light source to any available temperatures by adjusting current levels driving the light source.

In some embodiments where, a heat control assembly includes a heat sink having cooling fins that are exposed to the stream of sample gas. In embodiments where the heating element includes an external heating component, the light source may be mounted in contact with a peltier element that in turn is in heat conductive relationship with the heat sink. In some embodiments, a thermistor may be included in the heat control assembly for sensing temperature of the heat sink and/or heating element itself and sending a control signal to the microprocessor. The thermistor output may then be used to determine when temperature adjustments are needed, and initiate such temperature changes using the available heating element(s) and/or cooling element(s).

The portion 12A of the beam 12 exits as beam 50. This exit beam 50 impinges on a (high sensitivity) photo detector 52. The signal passes through an amplifier circuit 56 and an analog-to-digital converter 58 that provides a digital signal to microcontroller 42.

Another portion 62 of the intensity of the beam 12A exits and impinges on a (low sensitivity) photo detector 64. The signal passes through an amplifier circuit 68 and an analog-to-digital converter 70 that provides a digital signal to microcontroller 42.

Another portion 12B of light beam 12 does not enter the measurement cell at all. Rather, it is reflected away from the cell by a mirror. This portion 12B impinges on a photo detector 32 that provides a signal. This signal, which provides a reference signal, is representative of the maximum intensity of the light beam 12. The signal passes through an amplifier circuit 36 and an analog-to-digital converter 38 that provides a reference digital signal to microcontroller 42.

By comparing the intensity of the signal associated with reflected beam 12B with the signal associated with bounced back-and-forth beam 12A that exits as beam 50, the concentration of $^{12}CH_4$ in the sample gas can be determined with great accuracy using microcontroller 42 and detected at a sensitivity down to a few parts per million or even, ideally, to a sensitivity of one or less than one part per million. Because the methane found in natural gas contains 1% of isotope 13, if the concentration of $^{12}CH_4$ is ≥200 ppm, then discrimination of $^{13}CH_4$ is achievable at a level of detection of 2 ppm.

Note the use of two separate exit beams 50, 62 to activate photo detectors 52, 64 respectively becomes important where $^{12}CH_4$ is present at a relatively high level in the sample gas. At high levels beam 12A can be, for all practical purposes, completely absorbed before it exists through aperture 48 and, therefore, provided insufficient intensity of the beam 12A for use in computing the percentage of $^{12}CH_4$. This problem is overcome by the use of the second exit beam 62 and photo detector 64. Because the second exit beam 62 travels a relatively short distance through the gas sample, the attenuation of the beam 62 occurs at a rate that can provide methane detection even when the percentage of methane in the test gas is many times higher than that which is detectable by photo detector 52. The use of two separate exit beams 50, 62, one having a short length light path through the gas sample and the other having a long length light path, provides a system wherein the range of concentration of methane that can be measured is greatly expanded.

Preferably, light source 14 is not energized by a steady state voltage to produce a steady state light beam 12 but rather pulsed with a saw tooth wave shaped current. Each pulsation of light source 14 generates a pulsed light beam 12 that varies in wavelength over a selected bandwidth. Each current pulse produces light that varies in wavelength above and below the wavelength that undergoes the greatest absorption of the specific gas the instrument is designed to detect.

Because light source 14 is energized by a particular pulsed current waveform, the resultant signals generated by photo detectors 32, 52 and 64 are characterized by that particular waveform. Therefore, within microcontroller 42, absorption is detected by electronically dividing the signal of photo detectors 52 and 64 by the signal of photo detector 32. Microcontroller 42 is additionally connected to the temperature regulating system 16 of the light beam source 14, such that control of the temperature of the light beam source 14 can be determined based at least in part on the results of the absorption detection also carried out at the microcontroller 42. Methods of controlling and changing the temperature of the light beam source 14 based on detected absorption at the microcontroller 42 are described in greater detail below with reference to FIGS. 3 and 5.

Referring now to FIG. 3, an example method of detecting a concentration of multiple gases using a single cell will be described. The method 300 depicted in FIG. 3 can be implemented with the system described above with reference to FIG. 1, for example. As discussed further below, the process allows the system of FIG. 1 to be dynamically adjusted to measure concentration of any gas capable of being detected by infrared absorption. The process of FIG. 3 may be performed by microcontroller 42 and/or any other combination of particularly programmed hardware, firmware, and/or software. Depending on the embodiment, the method of FIG. 3 may include additional or fewer blocks and/or the blocks may be performed in a different order than is illustrated.

Method 300 begins at block 305 as a light source is energized at a first selected temperature $T_{op(1)}$. As described above, the temperature $T_{op(1)}$ can be selected based on a known operating temperature of the light source that will produce light at a wavelength corresponding to an absorption peak of a first gas to be detected. At block 310, the light beam produced by the light source is split and passed through a gas sample. After the light beam is passed through the gas sample, the method 300 continues to block 315.

At block 315, the concentration level $C_{(1)}$ of the first gas is determined within the gas sample. Determination of the concentration of the first gas within the gas sample can be based on analyzing a signal produced by one or more photodetectors and/or other circuitry in communication with the photodetectors as described above with reference to FIGS. 1 and 2. In some aspects, the concentration may be determined in units of parts per million (ppm), parts per billion (ppb), percent by volume, or the like. When the concentration level of the first gas has been determined, the method 300 continues to block 320.

At block 320, the concentration level $C_{(1)}$ of the first gas within the gas sample is compared to a predetermined threshold or limit $Limit_{(1)}$. In some embodiments, $Limit_{(1)}$ can be a threshold expressed in units of concentration, such as ppm, and the calculated concentration level $C_{(1)}$ can be compared to the threshold $Limit_{(1)}$. In other embodiments, $Limit_{(1)}$ can be a threshold expressed in units of absorbance or other characteristic of an analog or digital signal. In such embodiments, the analog signal generated by the one or more photodetectors, or a digital signal generated at an analog-to-digital converter based on the analog signal, may be compared directly to the threshold $Limit_{(1)}$ without requiring conversion to a concentration value $C_{(1)}$. Once the concentration or absorbance-based signal indicative of concentration is compared to $Limit_{(1)}$, a microprocessor or other circuitry of the detection system can determine whether the concentration of the first gas within the gas sample is greater than or equal to a preselected detection threshold. If the detection system determines that the concentration of the first gas is greater than or equal to the preselected detection threshold, the method 300 continues to block 325. If the detection system determines that the concentration of the first gas is not greater than or equal to the preselected detection threshold, the method 300 continues to block 330.

At block 325, if a concentration of the first gas has been detected that is at least equal to the predetermined threshold, the level of concentration can be reported. For example, the detection system may provide a graphic, audible, or other indication of a detection of the first gas, such as on a display of the detection system. In another example, reporting the level may include recording a concentration value in a memory unit of the display system and may or may not include a notification to a user of the system. After the detected concentration level is reported, the method 300 continues to block 330. In some embodiments, the comparison of block 320 and reporting of block 325 is not performed by the method. For example, the current concentration of gas may be displayed to the user without comparing to a preset threshold.

In some embodiments, the system is configured to provide alerts to one or more users, such as when a predetermined concentration of a gas is detected. For example, a notification may be automatically communicated, such as in real time as they are detected by the system (which may be stationary or attached to a self-driving vehicle, for example) to a supervising user, such as a technician that is responsible for identifying/confirming gas leaks. Such communications may be automatically transmitted to the entity in one or more modes of communication, such as, for example, electronic mail, text messaging, and regular postal mail, to name a few. In certain modes of communication to the entity, the communication may be configured to automatically operate on the entity's electronic device. For example, the entity's mobile device may, upon receipt of the transmitted communication, activate a software application installed on the entity's mobile device to deliver the communication to the entity (e.g., a SMS viewer or application may automatically display information from the communication when received by the device or when the device is connected to the internet). Alternatively, the communication may activate a web browser and access a web site to present the communication to the entity. In another example, a communication may be transmitted to an entity's email account and, when received, automatically cause the entity's device, such as a computer, tablet, or the like, to display the transmitted communication or a link to take the entity to a webpage with additional account information.

At block 330, after the method 300 has either reported a concentration at block 325 or determined that the concentration is less than the threshold $Limit_{(1)}$ at block 320, the method 300 determines whether to continue sampling to detect the first gas within the gas sample. The determination to continue sampling for the first gas or not to continue sampling for the first gas can be based at least in part on the outcome of the comparison of block 320. For example, if the concentration was determined to be less than the threshold $Limit_{(1)}$ at block 320, the method 300 may continue sampling to detect the first gas within the sample gas. If the concentration was determined to be greater than the threshold $Limit_{(1)}$ at block 320, the method 300 may determine that additional sampling for the first gas should not be done. In certain embodiments, the method 300 may determine that additional sampling for the first gas is required after detecting a concentration greater than the threshold $Limit_{(1)}$ to enhance the accuracy of the detection of the first gas. If the method determines that continued sampling for the first gas is to be done, the method 300 returns to block 315 while the light source remains energized at $T_{op(1)}$ to continue sampling. If sampling to detect the first gas is not to be continued, the method 300 continues to block 335. In an exemplary embodiment, a detection system may be configured to continuously and/or repeatedly sample for the first gas by determining "yes" at block 330 each time it is determined at block 320 that the concentration of the first gas is less than the threshold, until a concentration above the threshold is detected. Once a concentration above the threshold is detected, the exemplary system determines "no" at block 330 and continues to block 335.

At block 335, the light source is energized to an operating temperature equal to $T_{op(2)}$. Depending on the embodiment, the light source may continue emitting light as the temperature of the light source is changed or may be turned off during the temperature transition. Once the light source is energized at $T_{op(2)}$, the beam continues to pass through the sample gas at block 340. At block 345, the concentration level $C_{(2)}$ of the second gas is determined within the gas sample. Determination of the concentration of the second gas within the gas sample can similarly be based on analyzing a signal produced by the one or more photodetectors and/or other circuitry in communication with the one or more photodetectors as described above with reference to FIGS. 1 and 2. When the concentration level of the second gas has been determined, the method 300 continues to block 350.

At block 350, the concentration level $C_{(2)}$ of the second gas within the gas sample is compared to a predetermined threshold or limit for the second gas $Limit_{(2)}$. Like $Limit_{(1)}$, $Limit_{(2)}$ can be a threshold expressed in units of concentration, such as ppm, and the calculated concentration level $C_{(2)}$ can be compared to the threshold $Limit_{(2)}$. In other embodiments, $Limit_{(2)}$ can be a threshold expressed in units of absorbance or other characteristic of an analog or digital signal. In such embodiments, the analog signal generated by the one or more photodetectors, or a digital signal generated at an analog-to-digital converter based on the analog signal, may be compared directly to the threshold $Limit_{(2)}$ without requiring conversion to a concentration value $C_{(2)}$. Once the concentration or absorbance-based signal indicative of concentration is compared to $Limit_{(2)}$, a microprocessor or other circuitry of the detection system can determine whether the concentration of the second gas within the gas sample is greater than or equal to the preselected detection threshold. If the detection system determines that the concentration of the second gas is greater than or equal to the preselected detection threshold, the method 300 continues to block 355. If the detection system determines that the concentration of the second gas is not greater than or equal to the preselected detection threshold, the method 300 continues to block 360.

At block 355, if a concentration of the second gas has been detected that is at least equal to the predetermined threshold for the second gas, the level of concentration can be reported. For example, the detection system may provide a graphic indication of a detection of the second gas, such as on a display of the detection system. In another example, reporting the level may include recording a concentration value in a memory unit of the display system and may or may not include a notification to a user of the system. After the detected concentration level is reported, the method 300 continues to block 360.

At block 360, after the method 300 has either reported a concentration at block 355 or determined that the concentration of the second gas is less than the threshold $Limit_{(2)}$ at block 350, the method 300 determines whether to continue sampling to detect the second gas within the gas sample. Similar to the determination to continue sampling for the first gas at block 330, the determination to continue sampling for the second gas or not to continue sampling for the second gas can be based at least in part on the outcome of the comparison of block 350. For example, if the concentration of the second gas was determined to be less than the threshold $Limit_{(2)}$ at block 350, the method 300 may continue sampling to detect the second gas within the sample gas. If the concentration was determined to be greater than the threshold $Limit_{(2)}$ at block 350, the method 300 may determine that additional sampling for the second gas is required to enhance the accuracy of the detection of the second gas. In other aspects, the method 300 may determine that the determined concentration of the second gas is reliable and determine that additional sampling for the second gas should not be done. If the method determines that continued sampling for the second gas is to be done, the method 300 returns to block 345 while the light source remains energized at $T_{op(2)}$ to continue sampling. If sampling to detect the second gas is not to be continued, the method 300 can return to block 305 to begin the detection process again.

Although the method 300 is described generally in terms of repeatedly sampling to detect a first gas and transitioning to detect a second gas once the first gas is detected, other embodiments may be configured to alternate sampling for a first gas and a second gas without requiring a first gas to be detected to initiate the transition. For example, in certain implementations, the method 300 can sample to detect a first gas for a set time period, such as 1 second, 3 seconds, 5 seconds, 10 seconds, or the like, then proceed to sample for the second gas for a similar time period, such as 1 second, 3 seconds, 5 seconds, 10 seconds or the like, then sample again for the first gas. This cycle may repeat indefinitely.

Each transition between sampling for the first and the second gas can be performed based on the expiration of the predetermined time period, independent of whether a detectable concentration of either gas was detected during the preceding time period.

In certain embodiments of the gas detection systems discussed herein, the systems may perform a method including moving a stream of sample gas from the environment through a confined testing area such as cell 10 within a detecting instrument; energizing a light source 14 at a first operating temperature to produce a first light beam 12 at a frequency that corresponds to a high degree of absorption by a first preselected gas; splitting the first light beam 12 into three components; passing a first component of the first light beam 12 to a first photo detector 32 for providing a first electrical signal indicative of the intensity of the first light beam 12; passing a second component of the first light beam 12 multiple times through the confined testing area and then to a second photo detector 52 for providing a second electrical signal indicative of a concentration measurement corresponding to a lower concentration level; passing a third component of the first light beam 12 over a reduced length exit beam path 62 through the confined testing area and then to a third photo detector 64 for providing a third electrical signal indicative of a concentration measurement corresponding to a higher concentration level; using the first, second, and third electrical signals for determining the concentration level of the first preselected gas in the stream of sample gas; energizing the light source 14 at a second open component of the second light beam 12 to the first photo detector 32 for providing a first electrical signal indicative of the intensity of the second light beam; passing a second component of the second light beam 12 multiple times through the confined testing area and then to the second photo detector 52 for providing a second electrical signal indicative of a concentration measurement corresponding to a lower concentration level; passing a third component of the second light beam 12 over a reduced length path 62 through the confined testing area and then to the third photo detector 64 for providing a third electrical signal indicative of a concentration measurement corresponding to a higher concentration level; and using the first, second, and third electrical signals for determining the concentration level of the second preselected gas in the stream of sample gas.

Figure 4:
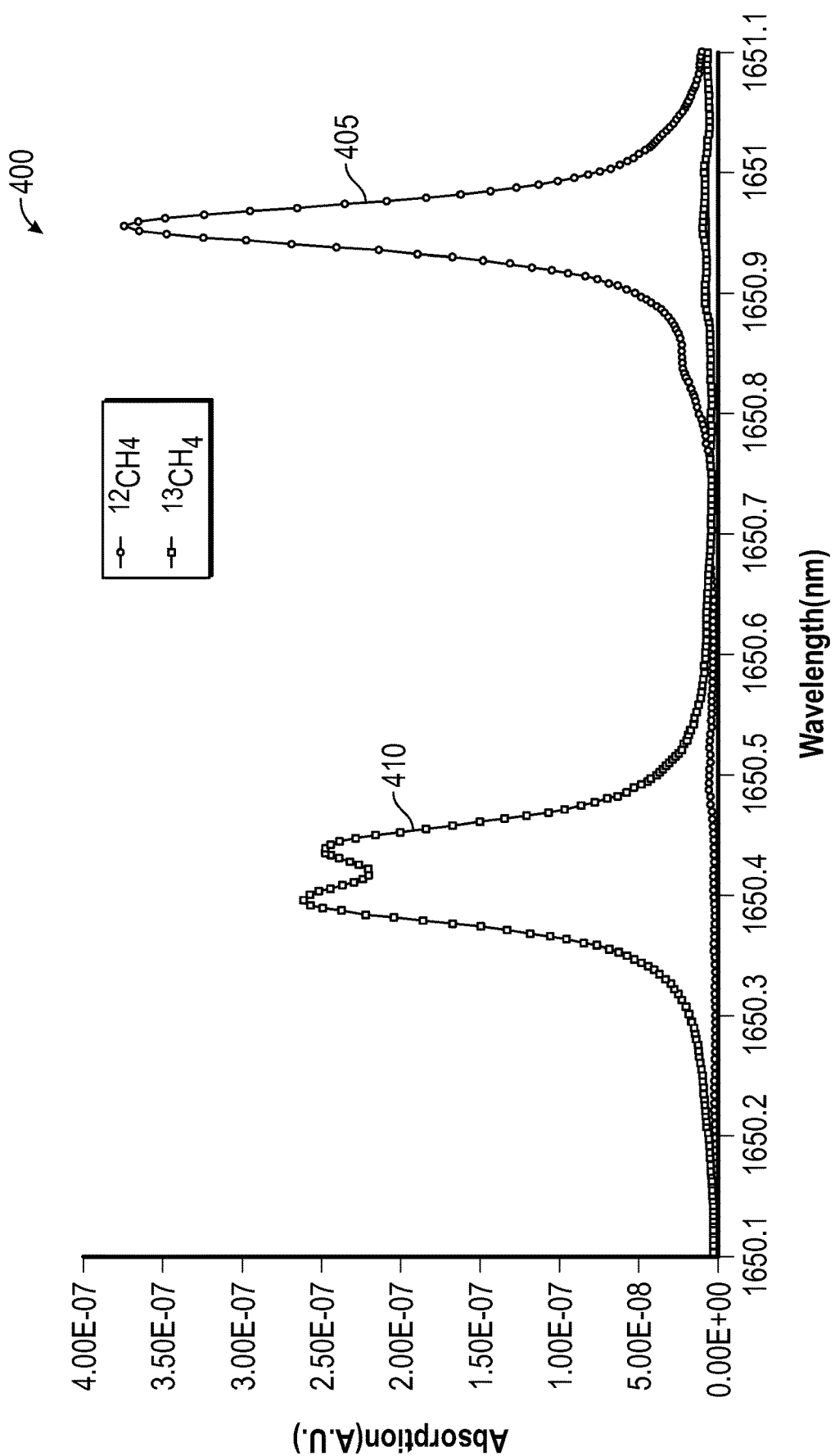
FIG. 4 is a portion of the absorption spectra of a first gas and a second gas in accordance with an exemplary embodiment.
Figure 5:
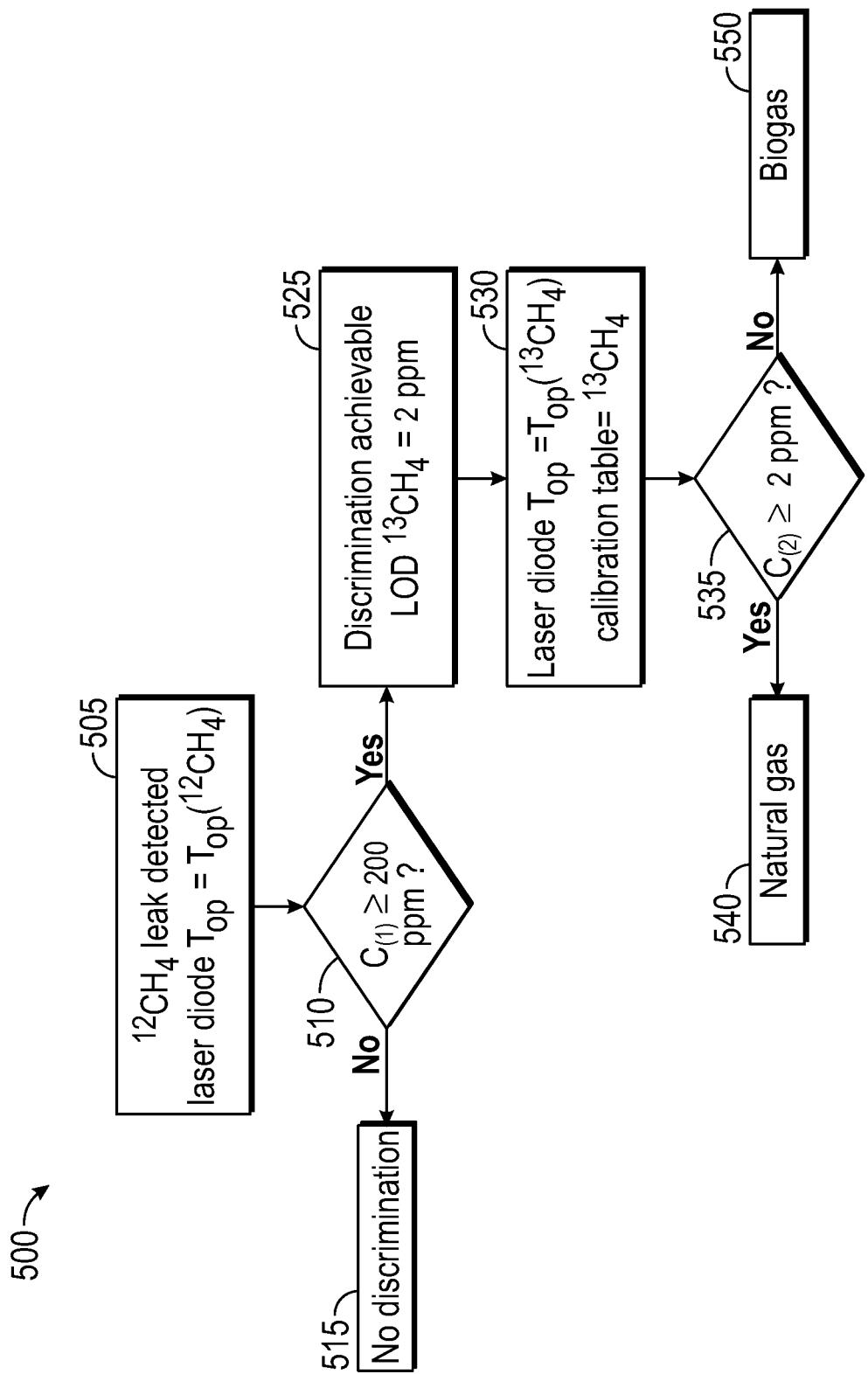
FIG. 5 is a flow diagram of an exemplary method of discrimination between a first and a second isotope of a gas.

Referring jointly to FIGS. 4 and 5, an example method of discriminating between a first and second gas will be described. In some embodiments, and by way of example only, the system and method can be used to discriminate between methane originating from a natural gas source and from a biogas source. Natural gas includes 82% to 95% of methane, with 99% of this methane being isotope C12 ("$^{12}CH_4$") and 1% being isotope C13 ("$^{13}CH_4$"). The methane found in biogas only includes isotope C12. Isotope C12 absorbs in near infrared in 1650.9 nm and 1653.7 nm. Isotope C13 absorbs in 1650.4 nm or 1653.1 nm. The infrared absorption spectra 400 in FIG. 4 depicts absorption of infrared by $^{12}CH_4$ and $^{13}CH_4$ between 1650.1 nm and 1651.1 nm. As shown in the spectra 400, $^{12}CH_4$ has an absorption peak 405 at approximately 1650.9 nm, while $^{13}CH_4$ has an absorption peak 410 at approximately 1650.4 nm. Accordingly, detection of absorption when a sample gas is exposed to infrared light having a wavelength of 1650.9 nm indicates the presence of $^{12}CH_4$, and the amount of absorption can determine the concentration of $^{12}CH_4$ within the sample. Similarly, detection of absorption when a sample gas is exposed to infrared light having a wavelength of 1650.4 nm indicates the presence of $^{13}CH_4$, and the amount of absorption can determine the concentration of $^{13}CH_4$ within the sample.

Accordingly, the example method 500 depicted in FIG. 5 can be used to detect methane and determine if the methane is from a natural gas source or a biogas source. Reference to components of a detection system throughout the description of the method 500 in FIG. 5 are with reference to the components as depicted in FIG. 1. To detect $^{12}CH_4$, the light beam source 14 is set to operate at $T_{op}=T_{op(12CH4)}$ at block 505 to produce a beam 12 having a wavelength λ that corresponds to high degree of absorption by $^{12}CH_4$. By way of example only, the light beam source 14 used in certain embodiments may be configured to produce a beam at approximately 1650.9 nm when operating at 25° C. In various embodiments, the appropriate operating temperature to produce a 1650.9 nm light beam can be determined for a particular light beam source based on the thermal and/or electrical properties of the light beam source. Beam 12 then exits the cell 10 and is measured by photodetectors 52, 64. In some embodiments, the measurement time can be 3 seconds, 5 seconds, 10 seconds, or similar. Once the beam 12 is measured by photodetectors 52, 64, the method 500 continues to block 510.

At block 510, the method 500 determines if the first gas is present in a concentration greater than or equal to a predetermined concentration threshold. In the example embodiment depicted, the threshold can be 200 ppm. If less than 200 ppm of $^{12}CH_4$ is detected (or some other predetermined concentration threshold), the method 500 proceeds to terminate at block 515 without performing a discrimination step. If 200 ppm or more of $^{12}CH_4$ is detected, the method proceeds to determine at block 525 that a sufficient concentration of methane is present in the sample gas to determine that a leak exits and/or to permit discrimination between natural gas and biogas. The threshold level of $^{12}CH_4$ can be determined, for example, based on a known limit of detection ("LOD") of the secondary gas to be detected. In one example, it may be known that the concentration of $^{13}CH_4$ in natural gas is expected to be approximately 1% of the $^{12}CH_4$ concentration, and the detector may have a limit of detection of approximately 2 ppm. Accordingly, the threshold for $^{12}CH_4$ can be determined to be 200 ppm, such that $^{13}CH_4$, if present, can be detected using the detector. In such systems, a concentration below 200 ppm of $^{12}CH_4$ likely could not be reliably evaluated for the presence of $^{13}CH_4$ because the $^{13}CH_4$ concentration, if present, is expected to be less than 2 ppm.

At block 530, the light beam source 14 shifts to operate at $T_{op(13CH4)}$, with the beam 12 having a wavelength λ that corresponds to high degree of absorption by $^{13}CH_4$. The particular shifting in temperature of the light beam source 14 to achieve the wavelength λ may be determined based on one or more algorithms and/or calibration tables. In a non-limiting example, if the light beam source described above produces a beam at 1650.9 nm when operating at 25° C., and dλ/dT of the light beam source is 0.1 nm/° C., the operating temperature corresponding to a beam at 1650.4 nm can be approximately 19-20° C. Preferably, the transition from $T_{op(12CH4)}$ to $T_{op(13CH4)}$ is relatively short, such as within 10 seconds, 5 seconds, or the like. Beam 12 again exits the cell 10 and is again measured by photodetectors 52, 62. Once the beam 12 is measured by photodetectors 52, 64, the method 500 continues to block 535.

At block 535, the method 500 determines if the second gas is present in a concentration greater than or equal to a second predetermined concentration threshold. In the example embodiment depicted, the second threshold can be 2 ppm. If 2 ppm or more (or some other predetermined concentration threshold) of $^{13}CH_4$ is detected, the method 500 terminates at block 540, where it is determined that the sample gas is from a natural gas source. If a concentration less than 2 ppm is detected, or if $^{13}CH_4$ is not detected at all, the method 500 terminates at block 550, where it is determined that the sample gas is from a biogas source. In various embodiments, the threshold for $^{12}CH_4$ can be greater or less than 200 ppm, and may be based at least in part on the ability of the system to detect low concentrations of a gas. For example, an initial threshold of 200 ppm may be selected where the system can reliably detect an infrared absorbing gas at 2 ppm and where the second gas or isotope comprises up to 1% of the gas.

After determining the source of the sample gas at block 540 or block 550, the method 500 can further include sending a notification. For example, a visual or audio indication of the source of the sample gas can be provided to a user of an analyzer or other apparatus performing the method 500 (e.g., a mobile device or display in communication with the analyzer and/or a remote computing device). In the example application of a gas company (or other entity) inspecting its infrastructure for leaks, a detection of methane, accompanied by a notification that the methane is from a biogas source rather than a natural gas source, can indicate that the detection of methane is not indicative of a natural gas leak. Similarly, a detection of methane accompanied by a notification that the methane is from a natural gas source can indicate that the detection of methane likely is indicative of a natural gas leak. Thus, the gas company can avoid wasting resources sending additional equipment and/or technicians to the site of the methane detection in the absence of a natural gas leak.

In another example, notifications may further include an indication that a first target gas has been detected, but at a concentration below the threshold for detecting the second target gas. In the example of a natural gas leak survey, a user can be notified of a "hit," indicating that methane has been detected, but at a level lower than the natural gas-biogas discrimination threshold (e.g., 200 ppm of $^{12}CH_4$ in the example of FIG. 5). Based on such notification, the user can be prompted to continue sampling in the area, as there may be a location nearby (e.g., closer to the source of the detected gas) where the concentration is higher and may exceed the threshold. Based on the notification the user can sample in additional locations within the vicinity of the initial notification until the analyzer detects a concentration of the first target gas above the predetermined threshold, samples for the second target gas, and notifies the user as to the outcome of the discrimination process. In some embodiments, a mobile analyzer may include a display that is continuously updated with the concentration level of the first gas, such as in relationship to the concentration level needed to discriminate between one or more constituent gases.

The embodiments described above are examples of the system and method. The following claims define the scope of the invention and include the full range of equivalents to which the recited elements of the claims are entitled.

The foregoing description details certain embodiments of the systems, devices, and methods disclosed herein. It will be appreciated, however, that no matter how detailed the foregoing appears in text, the devices and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated. The scope of the disclosure should therefore be construed in accordance with the appended claims and any equivalents thereof.

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

In general, the microprocessors and/or computing discussed herein may each include on or more "components" or "modules," wherein generally refer to logic embodied in hardware or firmware, or to a collection of software instructions, possibly having entry and exit points, written in a programming language, such as, for example, Java, Lua, C or C++. A software module can be compiled and linked into an executable program, installed in a dynamic link library, or can be written in an interpreted programming language such as, for example, BASIC, Perl, or Python. It will be appreciated that software modules can be callable from other modules or from themselves, and/or can be invoked in response to detected events or interrupts. Software modules configured for execution on computing devices can be provided on a computer readable medium, such as a compact disc, digital video disc, flash drive, magnetic disc, or any other tangible medium, or as a digital download (and can be originally stored in a compressed or installable format that requires installation, decompression or decryption prior to execution). Such software code can be stored, partially or fully, on a memory device of the executing computing device, for execution by the computing device. Software instructions can be embedded in firmware, such as an EPROM. It will be further appreciated that hardware modules can be comprised of connected logic units, such as gates and flip-flops, and/or can be comprised of programmable units, such as programmable gate arrays or processors. The modules or computing device functionality described herein are preferably implemented as software modules, but can be represented in hardware or firmware. Generally, the modules described herein refer to logical modules that can be combined with other modules or divided into sub-modules despite their physical organization or storage.

The term "non-transitory media," and similar terms, as used herein refers to any media that store data and/or instructions that cause a machine to operate in a specific fashion. Such non-transitory media can comprise non-volatile media and/or volatile media. Non-volatile media includes, for example, optical or magnetic disks, such as storage device. Volatile media includes dynamic memory, such as main memory. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

It is noted that the examples may be described as a process. Although the operations may be described as a sequential process, many of the operations can be performed in parallel, or concurrently, and the process can be repeated. In addition, the order of the operations may be rearranged. A process is terminated when its operations are completed. A process may correspond to a method, a function, a procedure, a subroutine, a subprogram, etc.

The previous description of the disclosed implementations is provided to enable any person skilled in the art to make or use the present disclosed process and system. Various modifications to these implementations will be readily apparent to those skilled in the art, and the generic principles defined herein may be applied to other implementations without departing from the spirit or scope of the disclosed process and system. Thus, the present disclosed process and system is not intended to be limited to the implementations shown herein but is to be accorded the widest scope consistent with the principles and novel features disclosed herein.

What is claimed is:

1. A method of measuring a concentration in an environment of at least a first preselected gas and a second preselected gas, the method comprising:
determining a temperature of a light source of a detection system;
based on the determined temperature, initiating activation of a cooling or a heating component associated with the light source to adjust the temperature to a predetermined first operating temperature, wherein the first operating temperature is selected to produce a light beam from the light source at a first preselected wavelength for absorption by the first preselected gas;
when the temperature of the light source has reached the first operating temperature, accessing measurement data from an optical detector, wherein with the light source at the predetermined first temperature the detection system is configured to measure a first absorption of the light beam at the first preselected wavelength to provide an indication of a concentration of the first preselected gas within the sample gas;
continuing to sample the environment by accessing the measurement data until the concentration of the first preselected gas exceeds a predetermined threshold; and
responsive to the concentration of the first preselected gas exceeding the predetermined threshold:
initiating activation of a cooling or heating component associated with the light source to adjust the temperature to a predetermined second operating temperature, wherein the second operating temperature is selected to produce a light beam from the light source at a second preselected wavelength for absorption by the second preselected gas; and
when the temperature of the light source has reached the second operating temperature, accessing measurement data from the optical detector, wherein with the light source at the predetermined second temperature the detection system is configured to measure a second absorption of the light beam at the second preselected wavelength to provide an indication of a concentration of the second preselected gas within the sample gas.

2. The method of claim 1, wherein at least one of the first and second preselected gases is selected from the group consisting of methane ($CH_4$), ethane ($C_2H_6$), propane ($C_3H_8$), butane ($C_4H_{10}$), oxygen ($O_2$), hydrogen ($H_2$), nitrogen (N), water ($H_2O$), hydrogen fluoride (HF), hydrogen chloride (HCl), hydrogen bromide (HBr), hydrogen sulfide ($H_2S$), ammoniac ($NH_3$), ammonia ($NH_4$), carbon monoxide (CO), carbon dioxide ($CO_2$), nitrogen monoxide (NO), nitrogen dioxide ($NO_2$), sulfur hexafluoride ($SF_6$), tetrahydrothiophene ($C_4H_8S$), and tert-butyl mercaptan ($C_4H_{10}S$).

3. The method of claim 1, wherein the second preselected gas is an isotopologue of the first preselected gas.

4. The method of claim 3, wherein the first preselected gas and the second preselected gas are isotopologues of methane.

5. The method of claim 1, wherein the cooling or heating component is configured to adjust the temperature of the light source between the first operating temperature and the second operating temperature in less than 10 seconds.

6. The method of claim 1, wherein the light source is a laser diode.

7. The method of claim 1, wherein the light source is a light emitting diode.

8. The method of claim 1, wherein the optical detector is a photodetector.

9. The method of claim 8, further comprising determining a temperature of the photodetector and initiating a heating or cooling component associated with the photodetector to adjust the temperature of the photodetector to an operating temperature of the photodetector.

10. The method of claim 9, wherein the operating temperature of the photodetector is controlled based on at least one of the first and second operating temperatures.

11. The method of claim 1, wherein the detecting instrument further comprises a multi-pass cell.

12. The method of claim 1, wherein the predetermined threshold for the concentration of the first preselected gas is associated with a limit of detection of the detection system corresponding to the second preselected gas.

13. The method of claim 1, wherein the predetermined threshold for the concentration of the first preselected gas corresponds to a minimum concentration of the first gas for which the detection system can discriminate between the first preselected gas and the second preselected gas.

* * * * *